United States Patent
Selig et al.

[11] Patent Number: 6,126,630
[45] Date of Patent: Oct. 3, 2000

[54] APPARATUS FOR GUIDING A MEDICAL PROBE

[75] Inventors: Manfred Selig; Rudolf Ullrich, both of Eggenstein-Leopoldshafen; Albert Linder, Hagen, all of Germany

[73] Assignee: Forschungszentrum Karlsruhe GmbH, Karlsruhe, Germany

[21] Appl. No.: 09/390,645

[22] Filed: Sep. 7, 1999

Related U.S. Application Data

[63] Continuation-in-part of application No. PCT/EP98/02866, May 14, 1998.

[30] Foreign Application Priority Data

May 20, 1997 [DE] Germany .......................... 197 21 030

[51] Int. Cl.⁷ .................................................. A61M 1/00
[52] U.S. Cl. .............................................................. 604/30
[58] Field of Search .......................... 604/30, 31, 32–39, 604/43, 22, 20–21, 27, 65, 246, 247; 606/167–171

[56] References Cited

U.S. PATENT DOCUMENTS 5,191,881  3/1993  Beck .
5,295,956  3/1994  Bales et al. .
5,359,991  11/1994  Takahashi et al. .

FOREIGN PATENT DOCUMENTS 2 626 760   8/1989  France .
WO 94/22358  10/1994 WIPO .

*Primary Examiner*—John D. Yasko
*Assistant Examiner*—Manuel Mendez
*Attorney, Agent, or Firm*—Klaus J. Bach

[57] ABSTRACT

In an apparatus for guiding a medical probe into body cavities, a handle housing is provided consisting of inner, upper and lower modules. The inner module comprises a rinsing liquid supply and suctioning hose assembly, which can be removed and discarded after use. The lower housing part includes probe support and guide structures and the upper housing part includes operating slide members engaging the hoses of the hose assembly for controlling the flow through the hoses. It also includes means extending through the inner module and engaging the probe support in the lower module for axially moving the probe support and the probe retained therein. A two-lumina shaft extends from the apparatus in alignment with the probe and receives the probe, and flow communication structures are provided for interconnecting the two hoses with the lumina in the shaft.

5 Claims, 4 Drawing Sheets

APPARATUS FOR GUIDING A MEDICAL PROBE

This is a continuation-in-part application of international patent application PCT/EP98/02866 filed May 24, 1998 which designates the U.S. and claims priority of German patent application 197 21 030.9 filed May 20, 1997.

BACKGROUND OF THE INVENTION

The invention relates to an apparatus for guiding a medical probe into body cavities, including means for rinsing the cavities with rinsing liquids and for sucking the rinsing liquids back into the probe. A housing is provided which includes connections for a rinsing liquid supply line and a suction line for removing the rinsing liquid and a guide channel for slideably supporting the probe.

The invention is concerned with the guiding of probes, for example, laser-coagulation-argon-or cementing probes which include rinsing means and means for sucking and the rinsing liquids through, or along, the shaft of the probe. In such arrangements, only a probe which utilizes a rinsing liquid and which, at the same time, is capable of suctioning out the rinsing liquid, provides for the best operating results. For example, during bi-polar coagulation the rinsing generally prevents carbonizations. Also, a laser beam can be carried by a water beam. It should however be possible to control the rinsing and the guiding of the probe directly at the probe support structure.

WO 94/05200 discloses such an apparatus, wherein, however, the rinsing and suction liquid volume is controlled from outside the probe support structure at a separate pumping apparatus. The probe support structure itself does not permit the control of the liquid flow volume so that it is relatively complicated to control all the functions at the same time. In addition, the whole apparatus must be cleaned and disinfected after each use or it must be discarded.

A rinsing arrangement alone for surgical apparatus is known from EP 642 800, which includes an elastic hose which guides the rinsing fluid and which can be pinched by keys that have to be held down for interrupting the rinsing fluid flow. This arrangement, however, cannot easily be combined with the apparatus according to WO 94/05200. Also, surgical procedures cannot be performed with this arrangement and the arrangement furthermore is not intended for such applications.

WO-A-94223358 discloses an arrangement for guiding a medical probe for body cavities, which includes a housing with means for rinsing and suctioning and rinsing liquids. The arrangement comprises several modules which are combined in a handle and which can be partially separated from one another.

It is the object of the present invention to provide a device for guiding a medical probe including rinsing means and means for suctioning out a rinsing liquid, wherein the rinsing liquid flow volume and the suction flow volume can be controlled directly at the device in simple manner. The number of parts, which are contaminated during the procedure should remain as small as possible in order to reduce decontamination expenses.

SUMMARY OF THE INVENTION

In an apparatus for guiding a medical probe into body cavities, a handle housing is provided consisting of inner, upper and lower modules. The inner module comprises a rinsing liquid supply and suctioning hose assembly, which can be disconnected and removed after use. The lower housing part includes probe support and guide structures and the upper housing part includes slideable operating members engaging the hoses of the hose assembly for controlling the flow through the hoses. It also includes means extending through the inner module and engaging the probe support in the lower module for axially moving the probe support and the probe retained therein. A two lumina shaft extends from the apparatus in alignment with the probe and receives the probe and flow communication structures are provided for interconnecting the two hoses with the lumina in the shaft.

The invention will be described below in detail on the basis of the accompanying drawings.

DESCRIPTION OF PREFERRED EMBODIMENTS

The various figures show a device for guiding a medical probe 43 for insertion into body cavities, wherein control means are provided for rinsing the cavities with a rinsing liquid and for suctioning out the rinsing liquid. The control means are included in a housing which also has connections for the rinsing and suctioning contents for the rinsing liquid.

Figure 1:
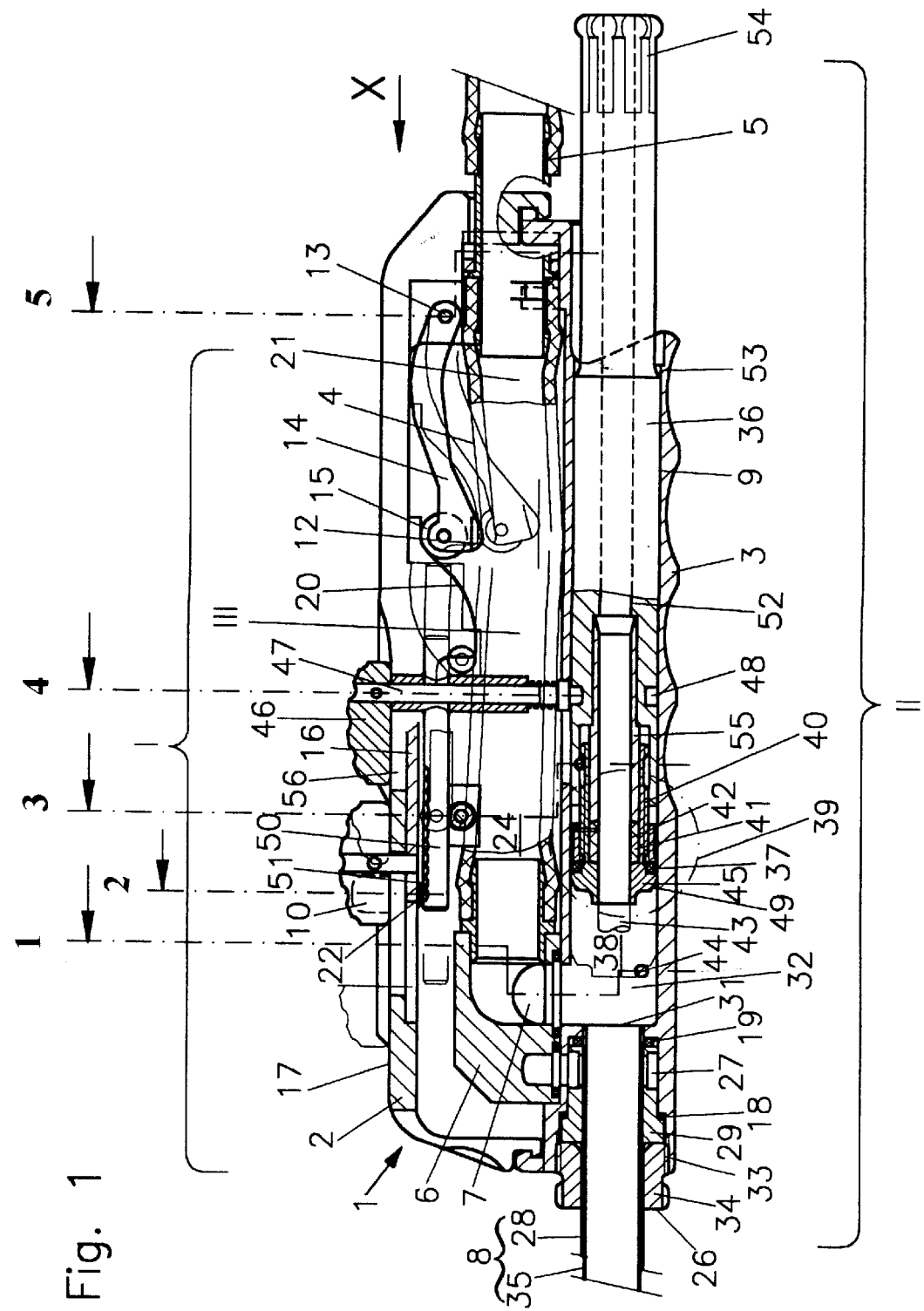
FIG. 1 is a cross-sectional view of a first embodiment of the invention.
Figure 4:
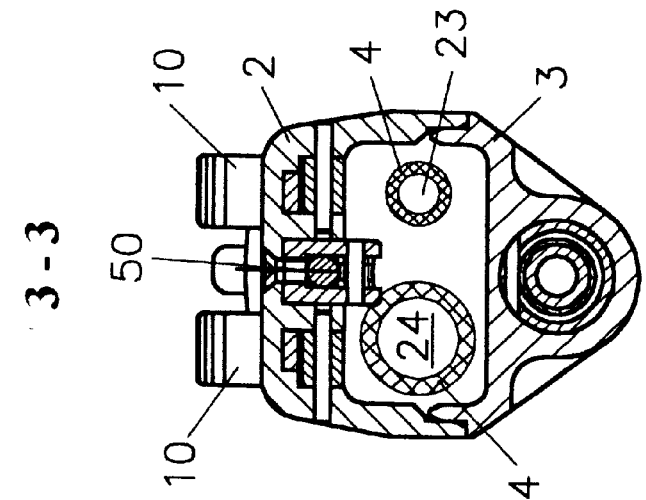
FIG. 4 is a cross-sectional view taken along line 3—3 of FIG. 1.

As shown in FIG. 1, the device comprises an upper module I, a lower module II and an inner module III, which are combined in a handle 1 consisting of an insulating material. The various parts can easily be separated from one another for cleaning and for exchanging parts. The inner module III consists of two flexible hoses 4, which have the same or different diameters, for rinsing and suctioning. Each is provided with a connector 5 at the proximal end and an angled transition piece 6 at the distal end of the hoses 4. The hoses 4 with the connection forming the module III can be discarded after use. After removal of the modules I and II, the module III can be easily removed or inserted. As a result, after reattachment of the upper housing part 2 (module I) and the lower housing part 3 (module II), a handle is formed in which the hoses 4 of the module III are supported in a form-locking fashion. They are axially firmly engaged and do not change their positions when external forces are acting on the hoses.

For controlling the flow through the hoses of the inner module III, the upper module I includes two longitudinally movable flow control slides 10, which are disposed on the outside and are operable by hand. By way of a mechanism which will be described later, the flow cross-section of the hoses 4 can be increased or decreased for controlling the flow volume during the rinsing and suctioning procedure upon movement of the slides by a thumb.

The lower module II includes a longitudinal channel 9 into which a probe receiver 36 having a through-bore 52 is inserted from the proximal end so as to be longitudinally slideably, but lockably supported by the probe receiver 36. FIG. 1 shows the probe receiver 36 in a retracted position. When moved forwardly, it abuts a transverse pin 44, which is disposed in a front portion 32 of the channel 9 and whose function will be explained later. For moving the probe receiver 36 in the longitudinal channel 9, an additional hand-operated intermediate slide 46 is disposed on the upper part 2 of the upper module I. The longitudinal channel 9 is open at its distal end adjacent the transition and suction passage 7 of the angled transition piece 6 toward the probe receiver 36 by way of the space 38, which is contaminated during operation of the probe. However, this space 38 is arranged between the hollow screw 45 which is screwed, with its threaded portion 41, into the distal end of the probe receiver 36 and which extends into the longitudinal channel 9 and is sealed by an adjustable seal 37 toward the proximal end 53.

The probe 43 is inserted into the through-bore 52 of the probe receiver 36 from the proximal end thereof and can be held in position with a variable retaining force. The clamping and sealing of the probe 43 in the through-bore 52 is accomplished by way of clamping structure 39 by rotating a rotatable handle 54, which is arranged at the proximal end of the probe receiver 36. The clamping structure 37 is arranged at the distal end of the probe receiver 36 in order to prevent contamination. It consists essentially of an annular elastic insert 41 with an opening. The annular elastic insert 41 is placed into the hollow screw 45 around the probe 43. Upon rotation of the screw 45 relative to the probe receiver 36 by the threaded portion 40, the insert 41 is pressed against the distance holder 55 in the probe receiver 36, whereby the receiver bore 42 is tightened around the probe 43 or widened depending on the direction of rotation. As a result, the probe 43 is either freely slideable within the bore 52 or it is firmly engaged within the probe receiver 36. This tightening and widening of the receiver bore 42 is also possible when the probe receiver 36 is fully inserted since the hollow screw 45 abuts the transverse pin 44 which prevents it from rotating while the probe receiver 36 is rotated by the rotatable handle 54. In this way the probe receiver generates an axial force onto the insert 41, whereby the diameter of the receiver bore 42 is reduced.

As already mentioned, an intermediate slide 46 is disposed on the top part 2 of the upper module I for moving the probe receiver 36 in the longitudinal channel 9. The slide 46 is disposed on a spring-loaded pin 47, which extends downwardly through a slot 50 in the upper housing part 2 between the hoses 4 and whose lower end extends into a circumferential groove 48 formed in the probe receiver 36. As a result, the probe receiver 36 can be moved back and forth by the slide 46. Upon lifting of the pin 47, the probe receiver 36 is disengaged from the pin 47 and can be pulled fully out of the longitudinal channel 9. Since the hollow screw 45 is provided at its front end with inclined surface areas 49, the spring loaded pin 47 is pushed back when the probe receiver is inserted into the longitudinal channel 9 and then snaps into the groove 48. Since the groove 48 is a circumferential groove, the probe receiver 36 can be rotated about its axis when it is installed which is important, for example, in connection with coagulation probes for arranging them in a proper angular orientation.

Figure 3:
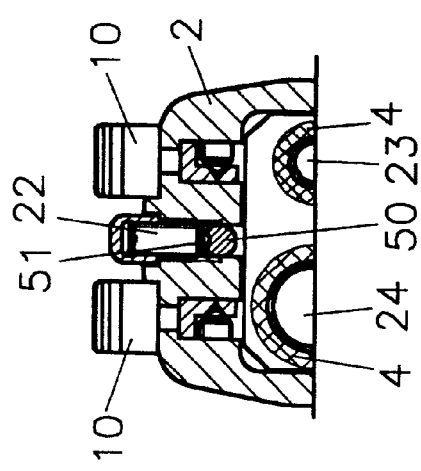
FIG. 3 is a cross-sectional view taken along line 2—2 of FIG. 1.

Parallel to the longitudinal channel 9 and normal to the pin 47, a bolt 50 with recesses 51 is supported in the upper housing part 2 so as to be longitudinally slideable. It is attached to the pin 47 such that it can be moved axially by the slide 46 together with the pin 47. A spring-loaded pin 22 engages the recesses 51 of the bolt 50 (see FIG. 3, for details) so that the probe receiver 36 can be arrested in several stop positions. A probe engaged by the probe receiver 36 can therefore repeatedly be brought to its proper operating position.

As already mentioned, the upper housing part 2 includes two longitudinally movable flow control slides 10 by which the flow through the hoses 4 of the inner module III can be controlled. The flow control slides change the cross-sections of the hoses 4 for controlling the flow volume during the rinsing and suctioning procedures. They are arranged on the top side 17 of the upper housing part 2 and extend parallel to the longitudinal axis 21 of the hose so as to be longitudinally movable thereon. Because of the symmetrical arrangement of the three slides 10, 46 the handle can be used equally well by right and left handed persons. All three slides can be operated by a single hand, that is the hand, which holds the handle. Each slide 10 acts on the respective hose 4 in the same way, either on the smaller diameter hose, which includes the rinsing lumen 23 or on the larger diameter hose, which includes the suction lumen 24: Upon movement of the slides, rollers 15 are engaged by control cams 11 and 20, which press the levers 14 with slide edges 12 against the hoses 4. Alternatively rollers may be used which engage the hoses directly and press them for example against an inclined surface for changing their flow cross-section.

The distal end of the handle includes a connection 26 for sealingly mounting various hollow shafts, which are exchangeable. In the embodiment as shown in FIG. 1, an outer sleeve 28 is provided which encloses an inner tube 35. As a result, a two-lumina hollow shaft 8 is provided wherein, as mentioned earlier, the larger lumen 24 is the suction lumen formed between the probe 43 and the inner tube 35 and the smaller lumen 23 is the rinsing lumen formed between the inner tube 35 and the outer sleeve 28. Into this inner tube 35, the probe 43 is inserted from the proximal end of the handle. The longitudinal channel 9 terminates in the inner tube 35, which is attached in the distal end of the lower module II and which is sealed therein by the seal 37 as mentioned earlier.

Figure 2:
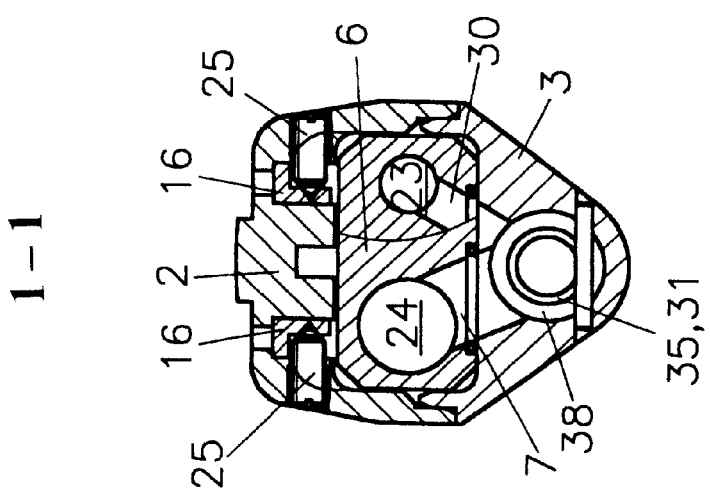
FIG. 2 is a cross-sectional view taken along line 1—1 of FIG. 1.
Figure 7:
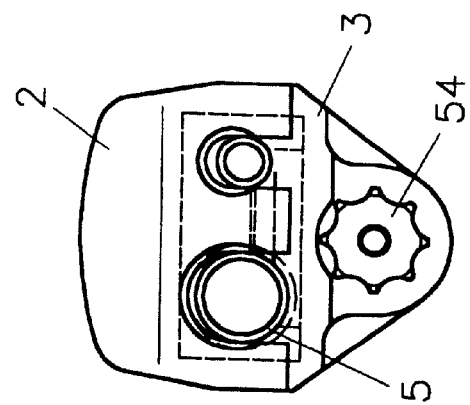
FIG. 7 is a view of the device in the direction x as indicated in FIG. 1.
Figure 6:
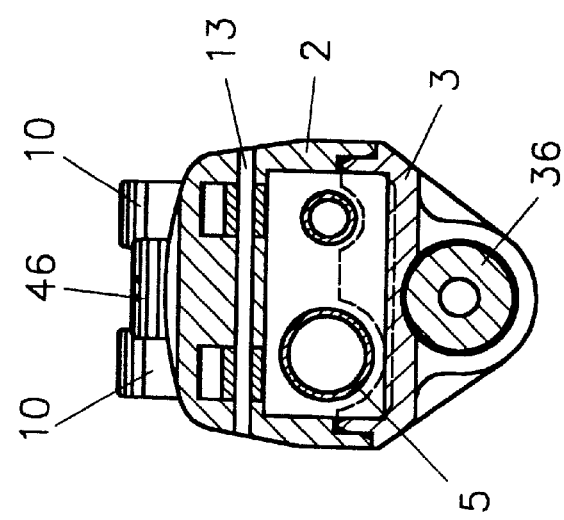
FIG. 6 is a cross-sectional view taken along line 5—5 of FIG. 1.
Figure 5:
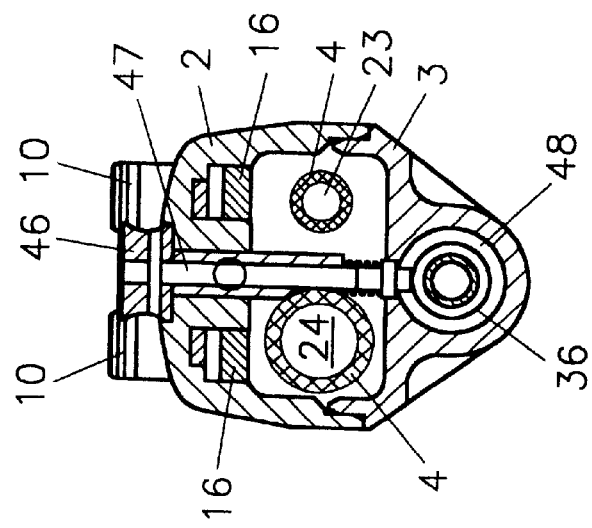
FIG. 5 is a cross-sectional view taken along line 4—4 of FIG. 1.
Figure 8:
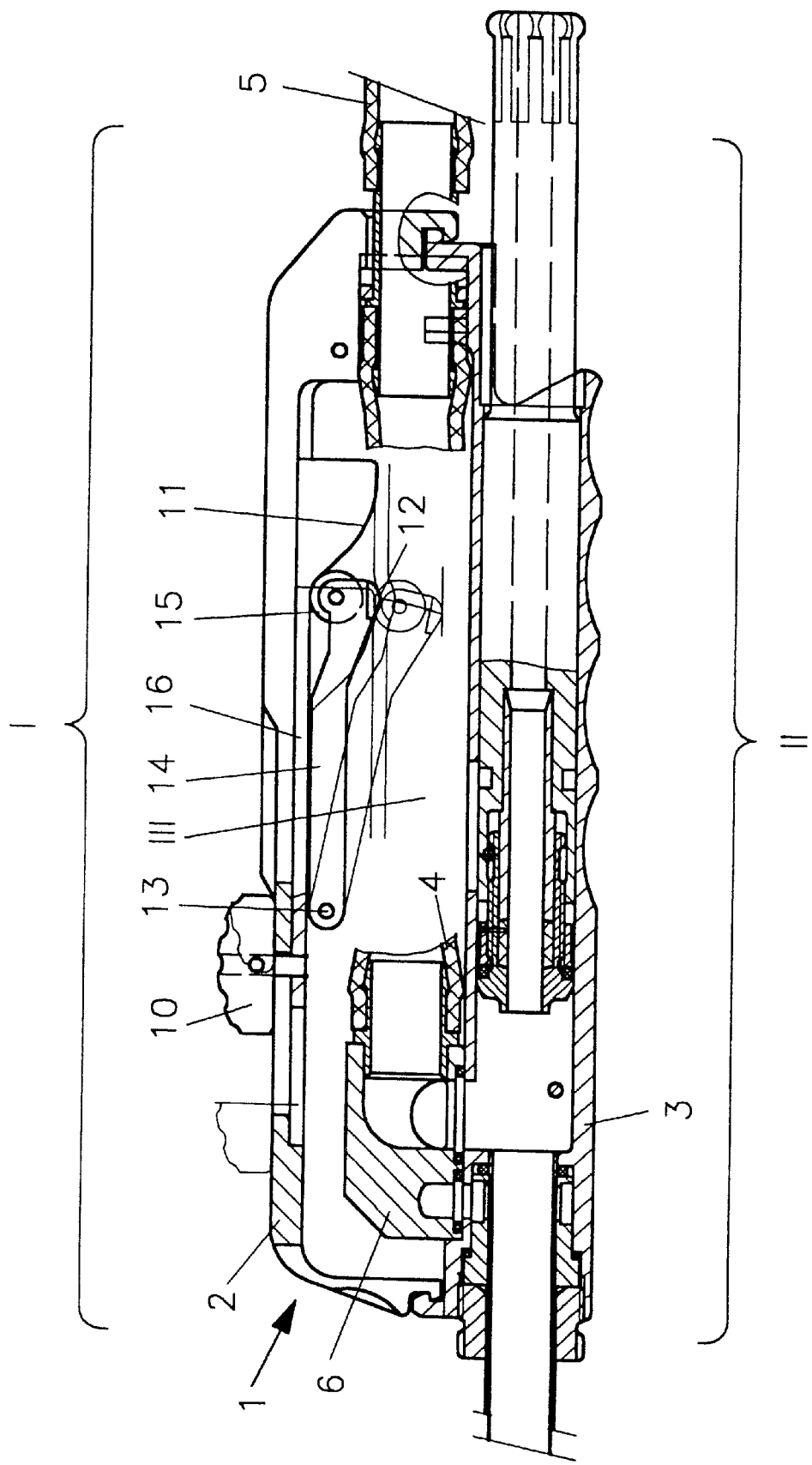
FIG. 8 shows a second embodiment of the device according to the invention.

The transition member 6 of the inner module III referred to earlier includes two separately sealed transition channels 7 and 30 in communication with the lumina 23 and 24 of the hoses 4. They lead to the two separate channels of the two-lumina hollow shaft 8 around the probe 43 as shown in FIG. 2. In another embodiment, which is not shown, the transition member 6 includes only one transition channel, which is connected to the hoses 4 and which leads to a single lumen shaft around the probe 43. The two lumina hollow shaft 8 as shown in the drawings is connected to the transition passages 7 and 30 in such a way that the smaller rinsing lumen 23 leads to the annular channel 27 of an end piece 29, which is sealingly connected to the outer sleeve 28 of the shaft 8. From this point, communication with the smaller one of the hoses 4 including the rinsing lumen 23 is established by way of the transition passage 30. The larger centrally arranged lumen 35 (inner tube) leads at the shaft end 31 to the longitudinal channel 9 from where communication with the larger lumen 24 of the hose 4 is established by way of the transition passage 7. The annular channel 27 is sealed with respect to the lower housing part 3 by two seals 18 and 19, which are biased in the axial direction of the shaft 8 by means of a nut 34 having a thread 33. The inner tube 35 by which the two lumina in the shaft are formed can be removed from the outer sleeve 28 for cleaning. The proximal seal 19 additionally seals the inner tube 35 with respect to the lower housing part 3. The connection 26 is such that also curved shafts can be used and rotated to the most suitable position in which they can be held by the nut 34.

In summary, it is pointed out that the arrangement provides for an instrument which is easy to disassemble as it consists of modules I and II including a probe holder 36 and a connection 26 permitting the utilization of different shafts, and an exchangeable hose unit forming the module III. The handle itself can be used repeatedly. Any parts with cavities, which are difficult to access, are designed as throw-away parts. As a result, the cleaning expenses are greatly reduced. The instrument permits a fine control of the flow volume for suction and rinsing. The movable parts of the suction and rinsing flow control structure do not come into contact with the rinsing liquid. They can therefore always remain in the handle. The flow control arrangement remains in any position that is, it does not need to be held in a particular position. The use of different hose cross-sections, the exchangeability of the shafts and the capability of operating with different probes and tools provides for a wide spectrum of applications for the instrument according to the invention.

What is claimed is:

1. An apparatus for guiding a medical probe into body cavities, said apparatus including a housing comprising several modules which, when combined, form a handle with connections for rinsing and suctioning lines and a guide channel for supporting said probe so as to be slideable and lockable in position in said guide channel, said housing enclosing an inner module comprising two flexible hoses, one for supplying rinsing liquid to said probe and the other for suctioning liquids from said probe, each of said hoses having a connecting piece at a proximal end and an angled transition pieces at the distal end, said inner module being designed as a throw away structure for single uses, an upper module disposed on top of said inner module and including hand operated flow control slides for controlling the flow through the hoses of said inner module, a lower module disposed below said inner module and including said guide channel, a probe receiver disposed in said guide channel so as to be axially slideable therein and including a through-bore for receiving and guiding said probe, said upper module including an intermediate slide having a pin extending through said inner module and engaging said probe receiver in said lower module for axially moving said probe receiver, said guide channel being in communication at its distal end with said angled transition piece, but being sealed with respect to said probe receiver, and an inner tube extending from said lower module and being arranged in axial alignment with said probe receiver for receiving said probe and being also in communication with the distal end of said guide channel such that an annular space between said probe and said inner tube is in communication with said hose for suctioning liquids from said annular space.

2. An apparatus according to claim 1, wherein said transition piece includes two separate passages each connected at one end to one of said hoses and at the opposite end to one of the lumina of a two-lumina shaft for said probe, said shaft comprising an outer sleeve and an inner tube disposed within said outer sleeve and receiving said inner tube receiving said probe, such that annular spaces are formed between said sleeve and said inner tube and between said inner tube and said probe, said annular spaces forming said lumina.

3. An apparatus according to claim 1, wherein said transition piece includes a passage connected at one end to a hose and at the opposite end to a lumen of the shaft of said probe, said shaft comprising a sleeve receiving said probe, whereby an annular space is formed between said sleeve and said probe to form said lumen.

4. An apparatus according to claim 2, wherein control cams are arranged on said flow control slides and levers are pivotally supported on said upper housing part and carry rollers disposed adjacent said control cams, said levers having edges disposed adjacent the hoses of said inner module, said control cams engaging said rollers so as to pivot said levers to force said lever edges against said hoses for squeezing said hoses when said flow control slides are moved in one direction for controlling the flow through said hoses.

5. An apparatus according to claim 4, wherein connecting pieces extend between said flow control slides and said cams and said connecting pieces are serrated and are engaged by engagement pins providing for a stepped engagement of said control sides when being moved along said housing top part.

* * * * *